United States Patent [19]

Bergwitz-Larsen et al.

[11] Patent Number: 4,536,495

[45] Date of Patent: Aug. 20, 1985

[54] NOVEL PHARMACEUTICAL COMPOSITION

[75] Inventors: Carl-Aage Bergwitz-Larsen, Vällingby; Rolf G. L. Österlund, Vallentuna, both of Sweden

[73] Assignee: KabiVitrum AB, Stockholm, Sweden

[21] Appl. No.: 472,295

[22] Filed: Mar. 4, 1983

[30] Foreign Application Priority Data

Mar. 12, 1982 [SE] Sweden ................................ 8201556

[51] Int. Cl.$^3$ ...................... A61K 31/70; A61K 31/14
[52] U.S. Cl. ........................................ 514/54; 514/642
[58] Field of Search ................................ 424/180, 329

[56] References Cited

U.S. PATENT DOCUMENTS 3,984,571 10/1976 Chen .................................. 424/362

OTHER PUBLICATIONS

J. Pharm. Sci., 50: 483–486, 1961.
J. Pharm. Sci., 52: 192–197, 964–967, 1963.
Lancet, Apr. 9, 1977, p. 810; Feb. 19, 1977 p. 424.
Chem. Abstrs., vol. 56: 7437g, 1962.
Chem. Abstrs., vol. 91: 128973r, 1979.
Chem. Abstrs., vol. 60: 3746, 1964.
Chem. Abstrs., vol. 58: 2324h, 1963.
Scrip Nos. 690 & 691, May 5 and 10, 1982, p. 18.

Primary Examiner—Albert L. Roberts
Assistant Examiner—John W. Rollins
Attorney, Agent, or Firm—Pollock, Vande Sande & Priddy

[57] ABSTRACT

A novel complex of carrageenan and a member of the group consisting of emepronium, doxycycline, and propranolol, pharmaceutical preparations containing such a complex, and its use in medicine.

16 Claims, No Drawings

NOVEL PHARMACEUTICAL COMPOSITION

FIELD OF THE INVENTION

The present invention relates to a novel complex of carrageenan and a member of the group consisting of emepronium, doxycycline and propranolol, and a process for the preparation thereof. The invention also relates to novel pharmaceutical compositions containing such a complex of carrageenan and active ingredient, a process for the preparation thereof and to the use of the complexes in medicine.

BACKGROUND OF THE INVENTION

Emepronium, which has the structural formula

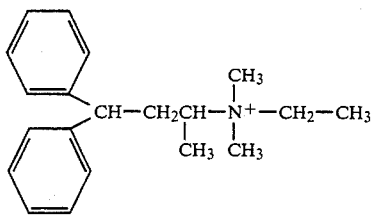

is a known therapeutically active substance which mainly is used in the form of its bromide. Its preparation is described e.g. in *Chemical Abstracts* 48, 729 a (1954). It is used as an anticholinergic and antispasmodic agent, mainly in the treatment of ailments related to the bladder function in man, for example incontinence, urinary frequency, irritable bladder, nervous bladder, and neurogenic bladder.

Doxycycline, which has the structural formula

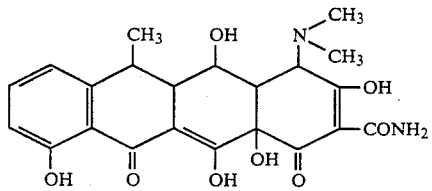

is also a known therapeutically active substance. It is mainly used in the form of its hydrochloride. It is used as an antibiotically active agent in the treatment of bacterial infections.

Also propranolol, which has the structural formula

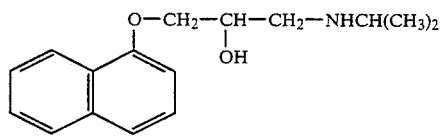

is a known therapeutically active substance. It is mainly used in the form of its hydrochloride. It is used as a betareceptor blocking agent.

The customary mode of administration of emepronium is by the oral route, mostly in the form of tablets which contain emepronium in the form of its bromide together with usual inert tabletting aids such as swelling agents. Patients taking emepronium bromide tablets are advised to swallow them with water. However, since patients suffering from bladder ailments at the same time often are advised to reduce their intake of fluid, there is a risk that the tablets are swallowed with too little water. The tablet may then, when disintegrating during its passage through the oesophagus, stick to the mucosa in the oesophagus whereby high local concentrations of emepronium bromide are created. Emepronium bromide has irritating effect on the mucosa, and such high local concentrations may cause severe irritation and ulceration in the oesophagus. Such effects have been described i.a. by Bennett, Oesophageal ulceration due to emepronium bromide, *Lancet* 1977, 1, 810. There is also risk for mouth ulcers caused by emepronium bromide.

A further problem with emepronium bromide is that it tastes very bitter. Liquid dose formulations are therefore accepted by the patients only with difficulty.

Also doxycycline and propranolol are mostly administered orally in the form of tablets containing doxycycline hydrochloride and propranolol hydrochloride. Also such tablets tend very easily to stick to the mucosa in the oesophagus giving the same type of irritation and ulceration as tablets containing emepronium bromide.

PRIOR ART

Certain complexes containing sulfated hydrocolloids, e.g. carrageenan, as complex forming agents are disclosed in the literature. Reference is made to French Pat. No. 5227M, *Journal of Pharmaceutical Sciences* Vol. 50 No. 6, 483–486 (1961); *Journal of Pharmaceutical Sciences* Vol. 52 No. 2, 192–197 (1963); and *Journal of Pharmaceutical Sciences* Vol. 52 No. 10, 964–967 (1963). However, it cannot be inferred from these citations that the novel complexes of the present invention would exhibit the properties of binding the active substance sufficiently strong in aqueous solution at the pH prevailing in the oesophagus that only a minor amount—for emepronium less than 3% of the amount of emepronium in a given complex—while the active substance is released very rapidly in the gastric juice, thus providing pharmacokinetic properties of the active substance which are quite comparable to the pharmacokinetic properties of the active substance in the presently used salt form.

DETAILED DESCRIPTION OF THE INVENTION

The present invention provides a novel complex of carrageenan and a member of the group consisting of emepronium, doxycycline and propranolol. These complexes, which are stable and chemically and physically well defined entities, represent an improvement over the presently used emepronium bromide, doxycycline hydrochloride and propranolol hydrochloride as is summarized below.

The complex of carrageenan and emepronium is only sparingly soluble in water. Therefore, the main part of emepronium will be complex-bound and biologically inactive during the passage of a corresponding tablet through the oesophagus. This greatly reduces the risk for irritation and ulceration of the mucosa in the oesophagus.

In the gastro-intestinal fluids, on the other hand, emepronium is rapidly released from its complex with carrageenan.

Therefore, the biological availability of the active substance is practically equivalent to the biological availability of conventional tablets containing emepronium bromide.

The novel complex of carrageenan and emepronium contains a sufficient amount of emepronium to make the preparation of tablets of suitable size possible. This is important because emepronium is often prescribed in large doses.

The complex also has suitable properties to admit its use in the preparation of tablets.

The complex of doxycycline and carrageenan, and of propranolol and carrageenan, have properties which are very much the same as outlined above for the emepronium-carrageenan complex. Thus, the carrageenan complexes of doxycycline and propranolol are only sparingly soluble in water. Therefore, the main part of the active substance will be complex-bound and biologically inactive during the passage of a corresponding tablet through the oesophagus. This greatly reduces the risk for irritation and ulceration of the mucosa in the oesophagus.

In the gastro-intestinal fluids, on the other hand, the active substance is rapidly released from its complex with carrageenan. Therefore, the biological availability also of doxycycline and of propranolol will be practically equivalent to the biological availability of conventional tablets containing doxycycline hydrochloride and propranolol hydrochloride.

The novel complex of carrageenan and doxycycline and propranolol, respectively, contains a sufficient amount of active substance to make the preparation of tablets of suitable size possible. The complex also has suitable properties to admit its use in the preparation of tablets.

The carrageenan-emepronium complex has a taste wherein the bad taste of emepronium is greatly reduced. The complex can therefore be used in aqueous oral preparations.

The nature of the carrageenan used to form the complexes of the invention is not any critical factor in the invention. The following specification and examples will, however, deal with complexes with a specific carrageenan, available under the trade name Aubygum x 2, which now will be identified.

Aubygum x 2 is manufactured by CECA SA, France, and is a carrageenan—a sulphated polysaccharide. Carrageenan is a hydrocolloid cell constituent of certain red seaweeds belonging to the Gigartinaceae family. The name carrageenan covers a range of sulphated polysaccharides which are composed of galactose residues.

Aubygum x 2 exists mainly as the sodium salt. It is a linear polysaccharide of sulphated galactose and 3,6-anhydrogalactose residues and exists in two principal fractions known as kappa and lambda amounting to about 50–80% and about 20–50%, respectively. The molecular weight is in the range 100,000–1,000,000.

IR Spectrum (KBr disc):

| Group Moiety | Band at wavenumber (cm$^{-1}$) |
|---|---|
| —O—H | 3700–3000 |
| aliphatic C—H | 3000–2800 |
| water | 1640 |
| S=O | 1300–1200 |
| C—O | 1100–1000 |
| C—O (anhydrogalactose) | 920 |
| S—O—C | 850 |

Presence of galactose and 3,6-anhydrogalactose: Apart from IR the presence of galactose and 3,6-anhydrogalactose can be established by thin-layer chromatography.

Appearance: White powder, odourless and tasteless.
Viscosity: 100–200 mPaS at 25° C. and not less than 5 mPaS at 75° C. using a Brookfield viscometer.
pH (1%, w/w, aqueous solution, 20° C.): 7–9.5
Optical rotation: $[\alpha]_D^{21} = 67.8°$ (c=0.1718, H$_2$O, Batch No. DjI 159).
Particle size: 98% through 250 μm sieve.
Moisture content: Not more than 12%, w/w, determined according to Karl Fischer.

Aubygum x 2 is a stable substance.

In clinical use the complexes of carrageenan and emepronium, doxycycline and propranolol, respectively, will normally be administered orally in the form of a pharmaceutical preparation which contains the active component optionally in combination with a pharmaceutically acceptable carrier. The carrier may be in the form of a solid, semisolid or liquid diluent, or a capsule. These pharmaceutical preparations are a further object of the invention. The complex may also be used without carrier material. Usually the amount of the complex is between 5 and 99% by weight of the preparation, for example between 25 and 80% by weight in preparations for oral administration.

In the preparation of pharmaceutical preparations containing the complex in the form of dosage units for oral administration, the complex may be mixed with a solid, pulverulent carrier, such as lactose, saccharose, sorbitol, mannitol, a starch such as potato starch, corn starch, or amylopectin, cellulose derivatives or gelatin, and may also include a lubricant such as magnesium stearate, calcium stearate or polyethyleneglycol waxes. The mixture is then pressed into tablets. If coated tablets are desired, a core prepared as described above may be coated with a concentrated sugar solution which may contain gum arabic, gelatin, talc, titanium dioxide or alternatively with a lacquer dissolved in volatile organic solvents or mixtures of solvents. To this coating various dyes may be added in order to distinguish tablets with different active compounds or with different amounts of the active compound present.

Soft gelatin capsules may be prepared which capsules contain a mixture of the complex and vegetable oil. Hard gelatin capsules may contain granules of the complex in combination with a solid, pulverulent carrier as lactose, saccharose, sorbitol, mannitol, potato starch, corn starch, amylopectin, cellulose derivatives or gelatin.

Liquid preparations for oral administration may be prepared in the form of syrups or suspensions, e.g. suspensions containing from 0.2% to 20% by weight of the complex, the remainder comprising for example sugar and a mixture of ethanol, water, glycerol and propylene glycol.

The dosage at which the complex is administered may vary within a wide range and will depend on various factors such as for example the individual requirements of each patient and the manner of administration. The dosages will be in the same ranges as ordinarily used for emepronium, doxycycline and propranolol. Thus, in general, oral dosages of emepronium will be in the range from 100 to 1600 mg/day; oral dosages of doxycycline will be in the range from 100 to 400 mg/day; and oral dosages of propranolol will be from 50 to 500 mg/day.

The following examples will illustrate the preparation of the complexes of the invention.

EXAMPLE 1

50 g emepronium bromide was dissolved in 800 g distilled water. 50 g carrageenan (Aubygum x 2) was added during stirring at room temperature. The mixture was stirred for 30 minutes and was thereafter allowed to stand for 2 hours. The mixture was decanted and the sediment suspended in 400 g distilled water. The mixture obtained was thereafter filtered through a cellulose filter under pressure. The humid filter cake was granulated through a 10 mesh sieve and was dried in an oven. The dry and sintered granulate obtained was ground to powder form.

EXAMPLE 2

70 g emepronium bromide was dissolved in 800 g distilled water. 50 g carrageenan (Aubygum x 2) was added during stirring at +30° C. The mixture was centrifugated at 4000 rpm. The solid residue was suspended in 200 g distilled water, whereafter the process was repeated. Hereafter the product obtained was granulated and dried as described in example 1.

EXAMPLE 3

50 g emepronium bromide was dissolved in 200 g distilled water. 50 g carrageenan (Aubygum x 2) was dissolved in 3.5 kg water at +30° C. The two solutions were separately filtered through deep filters. Thereafter the solutions were mixed and were stirred for 2 hours at +30° C. The mixture obtained was allowed to stand for 2 hours. The mixture was thereafter decanted and the sediment suspended in 400 g distilled water. The mixture obtained was filtered through cellulose filter under pressure. The filter cake thus obtained was granulated through a 10 mesh sieve, dried and ground to powder form.

EXAMPLE 4

10 g doxycycline hydrochloride was dissolved in 100 ml distilled water. 6,4 g carregeenan (Aubygum x 2) was added during stirring at room temperature. The slurry was stirred for 30 minutes and thereafter filtered through a cellulose filter under pressure. The filter cake was dispersed in 50 ml distilled water and the slurry was filtered as before. The humid filter cake was allowed to dry over night at +37° C.

The obtained powder was milled to a particle size below 63 μm. The powder was analyzed spectrophotometrically after dissolution in an aqueous acidic sodium chloride solution and contained 1.34 mmole doxycycline per gram.

EXAMPLE 5

10 g propranolol hydrochloride was dissolved in 100 ml distilled water. 9 g carregeenan (Aubygum x 2) was added during stirring at room temperature. The slurry was stirred for 30 minutes and thereafter filtered through a cellulose filter under pressure. The filter cake was dispersed in 500 ml distilled water and the slurry was filtered as before. The humid filter cake was granulated through a 10 mesh sieve and allowed to dry over night at +37° C.

The obtained powder was milled to a particle size below 200 μm. The powder was analyzed spectrophotometrically after dissolution in an aqueous sodium chloride solution and contained 1.69 mmole propranolol per gram.

As is illustrated in the above examples, the complexes of the invention are prepared by reacting a carrageenan or a salt thereof, with a solution of emepronium, doxycycline or propranolol, or a salt thereof, followed by isolation of the complex formed. Emepronium is suitably used as its bromide. Doxycycline and propranolol are suitably used as their hydrochlorides.

The emepronium-carrageenan complex can be prepared by choosing the relative amounts of carrageenan and emepronium so that the final complex will contain from 10 to 70% by weight of emepronium, expressed as emepronium bromide. Suitably the amount of emepronium bromide in the complex is from 50 to 70% by weight. The same ranges for the content of active substance apply also for doxycycline and propranolol.

Examples of usable salts of carrageenan that can be used are sodium salt and potassium salt.

The emepronium-carrageenan complex, herein also denoted emepronium carrageenate, obtained in examples 1–3 has the following characterizing data.

TABLE 1

Association characteristics of the binding of emepronium to Aubygum × 2

| Sample | Batch No | Sodium content[1] mmol/g on dry basis | Sulphate content[2] mmol/g on dry basis | Emepronium content[3] mmol/g on dry basis |
|---|---|---|---|---|
| Emepronium carrageenate | DjH 135 | 0.0 | 1.8[4] | 1.7 |

[1]Determined by atomic absorption spectrophotometry after dissolution of the samples in hydrochloric acid, 0.5 M.
[2]Determined gravimetrically as $BaSO_4$.
[3]Determined by extraction with bromothymolblue after dissolution in hydrochloric acid.
[4]Corresponding to 3.5 mmol/g based on Aubygum × 2.

IR spectra (KBr disc): The IR spectrum is given in Tables 2 and 3.

TABLE 2

Bands originating from Aubygum × 2

| Group moiety | Band at wavenumber (cm$^{-1}$) |
|---|---|
| —O—H | 3700–3000 |
| aliphatic C—H | 3000–2800 |
| water | 1640 |
| S=O | 1300–1200 |
| C—O | 1100–1000 |
| C—O (anhydrogalactose) | 920 |
| S—O—C | 850 |

TABLE 3

Additional bands originating from emepronium

| Group moiety | Band at wavenumber (cm$^{-1}$) |
|---|---|
| aromatic | 3100–3000 |
| aromatic ring | (1600) |
|  | 1490 |
| —CH$_3$ | 1450 |

Appearance: A white to yellowish and odourless powder.

Dissociation characteristics in NaCl and HCl: The exchange of emepronium by sodium as well as hydrogen ions was studied. Physiological conditions were used, i.e. 0.9%, w/w (0.15 mol/l) sodium chloride and 0.15 mol/l hydrochloric acid at 37° C. Different volumes of these solutions were tested. The experiments were performed in the following way: 170±1 mg of emepronium carrageenate (Batch No DjH 130) were shaken for 2 hours at 37° C. with 10.00 to 100.00 ml of the sodium chloride and hydrochloric acid solutions. After centrifugation and filtration through 0.2 μm filter the total content of emepronium in solution (expressed as exchanged emepronium) was determined. The results were that the dissolving effects of sodium and hydrogen ions were the same and that at least 50 ml were needed for complete dissolution of the sample.

It was calculated that the ratios [Na$^+$]/[emepronium] and [H$^+$]/[emepronium] must be $\geq 30$ for complete dissolution of emepronium carregeenate.

Solubility in water: The following procedure has been used: 340 mg of the sample (Batch No DjH 130) was shaken for 2 hours with 20.00 ml of deionized and distilled water. After filtration through 0.2 μm filter the solubility has been determined gravimetrically and by photometric determination of emepronium. The results are given in Table 4.

TABLE 4

| Solvent | ml of solvent | Amount of sample mg | Temp °C. | Solubility mg/ml gravimetr. | Solubility mg/ml photometr. |
|---|---|---|---|---|---|
| water | 20 | 340 | 25 | 0.5 | — |
| " | 50 | 170 | 21 | 0.07 | 0.03 |
| " | 50 | 170 | 37 | 0.2 | 0.08 |

The gravimetric results being higher than the photometric results, indicate that a minor amount of polysaccharide (probably as complex with emepronium) goes into solution. It is seen that the solubility in water of the complex is very low.

Melting point: 210°–230° C. (Mettler FP5).

Optical rotation: $[\alpha]_D^{21} = +40°(C=0.325, 0.9\%, w/w, NaCl, batch No. DjH 135)$ Total content of emepronium: 54–64%, w/w, (expressed as emepronium bromide).

Water-soluble emepronium $\leq 3\%$, w/w, of total content of emepronium expressed as emepronium bromide.

The following examples will illustrate the composition of pharmaceutical preparations containing the emepronium-carrageenate complex, the doxycycline-hydrocarrageenate complex, and the propranolol-hydrocarrageenate complex of the invention.

EXAMPLES 6 and 7

| COMPOSITION OF THE EMEPRONIUM CARRAGEENATE TABLETS | | |
|---|---|---|
| | Tablet Content (mg) | |
| Composition | 100 mg DKA 109 | 200 mg DKA 110 |
| Granulated emepronium carrageenate, < 200μ | 175 | 350 |
| Magnesium stearate | 4 | 8 |
| Colloidal silicon dioxide | 2 | 4 |
| Polyvinylpolypyrrolidone | 21 | 42 |
| Average weight | 202 mg | 405 mg |

EXAMPLE 8

Capsules

Emepronium carrageenate as prepared in Example 1 was filled in capsules, each capsule containing 350 mg granulated emepronium carrageenate.

EXAMPLE 9

Capsules

Emepronium carrageenate as prepared in Example 1 was filled in capsules, each capsule containing 175 mg granulated emepronium carrageenate.

EXAMPLE 10

Composition of doxycycline hydrocarrageenate tablets:

| Ingredients | Content per tablet |
|---|---|
| Doxycyclinehydrocarrageenate | 160 mg |
| Magnesium stearate | 4 mg |
| Colloidal silicone dioxide | 2 mg |
| Polyvinylpolypyrrolidone | 20 mg |
| Microcrystalline cellulose (Avicel ®) | 64 mg |
| Average tablet weight | 250 mg |

The tablets were produced by a direct compression technique.

EXAMPLE 11

Capsules

Doxycycline hydrocarrageenate as prepared in Example 4 was filled in capsules together with customary excipients, each capsule containing 100 mg doxycycline.

EXAMPLE 12

Composition of propranolol hydrocarrageenate tablets:

| Ingredients | Content per tablet |
|---|---|
| Propranolol hydrocarrageenate | 164 mg |
| Magnesium stearate | 4 mg |
| Colloidal silicone dioxide | 2 mg |
| Polyvinylpolypyrrolidone | 20 mg |
| Microcrystalline cellulose (Avicel ®) | 60 mg |
| Average tablet weight | 250 mg |

The tablets were produced by a direct compression technique.

EXAMPLE 13

Capsules

Propranolol hydrocarrageenate as prepared in Example 5 was filled in capsules together with customary excipients, each capsule containing 100 mg propranolol.

Besides emepronium, doxycycline and propranolol, other ulcerogenic drug substances of amine type, that is drugs containing one or more amine groups, can be complexed with carrageenans in order to obtain complexes having reduced ulcerogenic effects particularly in the oesophagus. The present invention includes also complexes of carrageenans with such compounds.

Biological tests

An in vivo comparative study on the oesophagus-irritating effect in dogs was made using 0.2 g tablets of emepronium carrageenate and 0.2 g tablets of Cetiprin ®, a commercially available emepronium bromide product. A further in vivo comparative study in cats was made using uncoated doxycycline hydrocarrageenate tablets, corresponding to 0.1 g of doxycycline hydrochloride, and coated doxycycline hydrochloride 0.1 g tablets. The latter tablets are commercially available Vibramycin ® tablets.

The experimental method is essentially as described by Carlborg and Densert, *Eur. surg. Res.* 12, 1980, 270-282.

MATERIAL AND METHODS

A. Test of emepronium carrageenate tablets

Test tablets

Emepronium carrageenate tablets corresponding to 0.2 g emepronium bromide, uncoated and film coated with Eudragit E, respectively, and Cetiprin ® 0.2 g tablets film coated with Klucel LF were tested in the present study.

The emepronium carrageenate tablets were prepared as illustrated in Examples 6 and 7.

The composition of the emepronium carrageenate tablets are essentially as given in Examples 6 and 7. The Cetiprin ® tablets were as commercially available.

Animals

Three male and three female Beagle dogs were used for the study. The body weights of the animals ranged from 10.3 to 14.4 kg. Two animals were examined per test tablet.

Experimental procedure

Dogs fasted overnight, were anaesthetized with pentobarbital intravenously at an induction dose of 30 mg/kg body weight. The animals were placed on their right side and kept under intravenous anaesthesia throughout the experiment. Before the administration of the drug the oesophagus was inspected by use of an endoscope to make sure that the mucous membrane was normal. Endotracheal intubation was also performed.

A thread was tied firmly round the tablet to be tested. The thread was winded around a polyethylene catheter and was then together with the catheter inserted into a feeding tube with the tablet tied at the end. Thereafter the tube was introduced into the oesophagus to a specified length. The tablet was deposited by slow withdrawal of the tube with the thread attached to the catheter passing through. The upper end of the thread was sutured to the angle of the lips. The upper end of the catheter was attached to an infusion pump. During the first hour of emepronium carrageenate tablet exposure, tap water (2-5 ml/h) was instilled into the oesophagus close to the tablet. The tablet was placed at the beginning of the distal third of the oesophagus. The deposition of the Cetiprin ® tablets was made in the same way but without insertion of a catheter for installation of water. The exposure time varied from 4.8 to 8 hours.

All animals were sacrificed at the end of the exposure period by means of overdosing pentobarbital. After sacrifice the oesophagus was dissected free and the external aspect was inspected. Thereafter the oesophagus was opened in situ. The site of the tablet was ascertained and the disintegration of the tablets as well as the dissolution/disruption of the film coat were recorded.

The following criteria were used for the assessment of the degree of disintegration of the tablets:
+ the external part of the tablet is moist
+ + the tablet is moist, swollen and/or soft but withstands gentle pressure
+ + + the tablet is dissolved, fallen apart or softened to an extent not to withstand gentle pressure.

The following criteria were used for the assessment of the degree of dissolution/disruption of the film coat.
— cracked
— — partly dissolved/removed
— — — almost completely dissolved/removed
— — — — completely dissolved/removed.

The oesophagus then was dissected free of adnexal tissue and spread on a cotton cloth. If necessary the oesophageal mucosa was gently rinsed with a few ml of physiological saline in order to verify if the tablet material was removable from the mucosal surface or if it stuck to the surface. In many cases the macroscopical appearance of the oesophagus at the site of the tablet as well as the tablet proper was recorded by photography. Thereafter the oesophagus was spread on a blotting paper on which appropriate markings were done as to the macroscopical characteristics of the oesophagus. Fixation was done in 10% buffered neutral formalin for 18-48 hours. Paraffin sections were prepared from at least two regions of the oesophagus accordingly: the oesophagus at the site of the tablet and a portion proximal to the site of the tablet. The paraffin sections, 4-5 microns thick were stained.

B. Test of doxycycline hydrocarrageenate tablets

Test tablets

The tablets tested were uncoated doxycycline hydrocarrageenate tablets prepared according to Example 10, corresponding to 0.1 g of doxycycline hydrochloride, and coated doxycycline hydrochloride 0.1 g tablets, commercially available Vibramycin ® tablets.

Animals

Eight female cats were used for the study. The body weight of the animals ranged from 2.0 to 2.6 kg.

Experimental procedure

The experimental procedure is as described above for the test on dogs. The exposure time for the tablets was 8 hours.

RESULTS AND COMMENTS

The disintegration of the emepronium carrageenate tablet corresponding to 0.2 g emepronium bromide, uncoated or coated, was complete after a deposition time of 4.8-6 hours.

Morphologically i.e. macroscopically and histopathologically, no oesophago-irritant effect was observed with the emepronium carrageenate 0.2 g tablets.

Cetiprin ® 0.2 g coated tablets deposited for 6-8 hours in the oesophagus were comparably disintegrated although no accelerated disintegration of the tablet was applied.

Cetiprin ® 0.2 g tablets produced a distinct oesophago-irritant effect in dogs exposed for 6 or 8 hours. After 6 hours the intensity of the changes was slight but after 8 hours were more pronounced. The changes consisted on one hand in a macroscopically visible oedema of the oesophageal wall and on the other hand in degenerative changes in the epithelial layer. The latter changes had a regional appearance and were seen as oedema with the spreading apart of epithelial cells in the dog that was exposed for 6 hours. In the dog that was exposed for 8 hours the oesophageal lesions in principle were of the same character but were more advanced with swelling and necrosis of epithelial cells.

The disintegration at 8 hours of the uncoated doxycycline hydrocarrageenate tablets corresponding to 0.1 g of doxycycline hydrochloride was +(+) or ++ (i.e. the tablet is moist, swollen and/or soft but withstands gentle pressure) in three of the four cats tested and +++ (i.e. the tablet is dissolved/fallen apart or softened to an extent not to withstand gentle pressure) in one cat.

The coated doxycycline hydrochloride (Vibramycin®) 0.1 g tablets were completely disintegrated at 8 hours and scored +++ in all the four cats tested.

The morphological investigation, which comprised macroscopic and histopathological examination of exposed oesophagi, did not reveal any pathological changes in the oesophageal mucosa or wall of cats after an exposure time of 8 hours with uncoated doxycycline carrageenate tablets corresponding to 0.1 g of doxycycline hydrochloride.

Consistent changes were found in all the cats after 8 hours of exposure with doxycycline hydrochloride (Vibramycin®) 0.1 g tablets. Macroscopically, the oesophagus was yellowish discoloured and slightly rigid and thin at the site of the tablet. The histopathological findings consisted in pronounced degenerative changes in the basal portion of the mucosa, slight oedema in the propria and focal necrosis of muscularis mucosae.

CONCLUSION

No local oesophageal-irritant effect of emepronium carrageenate tablets corresponding to 0.2 g emepronium bromide could be revealed using an in vivo dog model providing rapid and complete disintegration of the tablets.

No oesophageal-irritant effect of doxycycline hydrocarrageenate tablets corresponding to 0.1 g of doxycycline hydrochloride could be revealed using an in vivo cat model in which sufficient disintegration of tablets was achieved. With doxycycline hydrochloride (Vibramycin®) 0.1 g tablets, tested under identical conditions, severe morphological changes were observed in the oesophagus. Hence the conclusion is drawn that the new formulation of doxycycline, doxycycline carrageenate, offers significantly improved protection against oesophagoirritation as compared with the commercially available tablet.

Bioavailability

A bioavailability study of 0.2 g tablets of emepronium carregeenate and 0.2 g Cetiprin® tablets containing emepronium bromide was carried out on 9 healthy volunteers. It was found that the emepronium carrageenate 0.2 g tablets gave the same serum peak time as the commercially available 0.2 g Cetiprin® tablets and that emepronium from the emepronium carrageenate tablets was absorbed essentially to the same extent as judged by serum concentration and urinary excretion data. The two formulations were considered bioequivalent.

Dissolution rate of doxycycline hydrocarrageenate

The dissolution rate according to USP XX in chloride buffer, pH 1.2 at +37° C. of doxycycline hydrocarrageenate was compared to the dissolution rate of doxycycline hydrochloride, using the same procedure. The result was that the dissolution rate of the active substance was virtually undistinguishable between the two preparations. This result indicates that the doxycycline hydrocarrageenate complex of the invention releases the active substance in the gastric juice at the same rate as the commercially available preparations containing doxycycline hydrochloride.

What we claim is:

1. A complex of carrageenan and 10–70% by weight of said complex of emepronium, calculated as emepronium bromide.

2. A complex according to claim 1 in solid form.

3. A complex according to claim 1 in dried form.

4. A method for the treatment of ailments related to the bladder function in man, by administering to a host in need thereof of a therapeutically effective amount of a carrageenan-emepronium complex according to claim 1.

5. The method of claim 4 which comprises orally administering said complex to provide 100–1600 mg/day of said emepronium.

6. A complex according to claim 1 containing 50–70% by weight of emepronium, calculated as emepronium bromide.

7. A pharmaceutical preparation comprising a pharmaceutical carrier and in an amount effective for treating bacterial infections or bladder ailments a complex of carrageenan and 10–70% by weight of said complex of emepronium, calculated as emepronium bromide.

8. A pharmaceutical preparation according to claim 7 in a form intended for oral administration.

9. The pharmaceutical preparation of claim 8 which is an aqueous liquid suspension containing 0.2% to 20% by weight of said complex.

10. A pharmaceutical preparation according to claim 7 in dosage unit form.

11. A pharmaceutical preparation according to claim 10 in tablet or capsule form.

12. A pharmaceutical preparation according to claim 7 in the form of an aqueous liquid preparation.

13. A pharmaceutical preparation according to claim 12 in the form of an aqueous suspension.

14. A process for the preparation of a complex of carrageenan and 10–70% by weight of said complex of emepronium, calculated as emepronium bromide; which comprises reacting in solution carrageenan or a salt thereof with emepronium, or salt thereof, to, thereby provide said complex.

15. A process according to claim 14, wherein the complex formed is isolated and dried.

16. The process of claim 14 which comprises reacting the sodium or potassium salt of carrageenan and emepronium bromide.

* * * * *